United States Patent [19]

Siepser

[11] Patent Number: 4,556,998

[45] Date of Patent: Dec. 10, 1985

[54] ARTIFICIAL INTRAOCULAR LENSES AND METHOD FOR THEIR SURGICAL IMPLANTATION

[76] Inventor: Steven B. Siepser, 119 Devon Rd., Paoli, Pa. 19301

[21] Appl. No.: 520,187

[22] Filed: Aug. 4, 1983

[51] Int. Cl.$^4$ .............................................. A61F 1/16
[52] U.S. Cl. ...................................................... 623/6
[58] Field of Search ............................................. 3/13

[56] References Cited

U.S. PATENT DOCUMENTS

| | | | |
|---|---|---|---|
| 4,092,743 | 6/1978 | Kelman | 3/13 |
| 4,316,292 | 2/1982 | Alexeev | 3/13 |
| 4,449,257 | 5/1984 | Koeniger | 3/13 |

*Primary Examiner*—Richard J. Apley
*Assistant Examiner*—James Prizant
*Attorney, Agent, or Firm*—Eugene E. Renz, Jr.

[57] ABSTRACT

Improved artificial intraocular lenses for surgical implantation to replace a damaged natural lens in an otherwise functional eye of a patient are described; the improvement comprising forming the lens, so as to have a minimum diameter of about 2 mm and a maximum diameter of about 5 mm prior to implantation, which is less than the diameter of the natural lens, from a dry, solid, hydrophilic material capable of being hydrated by the natural fluid in the eye to expand after implantation to provide an optically correct lens having a suitable diameter from about 6 mm to about 14 mm, to permit implantation of the lens through an incision of minimal length corresponding to the diameter of the dry lens and thus restoring the vision of the patient with minimal trauma. The invention also includes the improved method of implantation through an incision of minimal length.

14 Claims, 5 Drawing Figures

ARTIFICIAL INTRAOCULAR LENSES AND METHOD FOR THEIR SURGICAL IMPLANTATION

BACKGROUND

The lenses of human and animal eyes are subject to damage by physical or other external trauma whether accidental or otherwise and by the formation of cataracts. It has been common practice for many years to surgically remove such damaged lenses. An eye with the lens removed is said to be in the aphakic condition. Subsequent to intracapsular or extracapsular lens extraction, the aphakic eye does not have the ability to focus light with the result that the retina receives only a blurred image. Contact lenses, spectacles or a combination of the two have been used in the past with varying degrees of success to focus the light rays to restore vision. The use of contact lenses and eye glasses to overcome aphakia is subject to the fundamental drawback that such devices are located outside of the eye which results in a shift of the optical center from the natural position within the eye. This results in distortion and/or a change in size of the image. Moreover, eyeglasses cannot restore normal binocular vision if the other natural eye remains and contact lenses must be in continuous use to maintain vision in the aphakic eye.

Cataracts are the most common disorder of the eye and are the second leading cause of blindness in the United States. A cataract is a biochemical change in the structure of the lens of the eye which causes transformation of the normal transparent lens to a cloudy or opaque state. The function of the lens is to focus light rays to form a perfect image on the retina. Cataracts interfere with the focusing of the light rays causing the image to become blurred and eventually leading to blindness if unattended. The opacities caused by cataracts are often not distributed uniformly so that the lens has both opaque and clear areas. Therefore, the degree of loss of vision depends on the size, location and densities of the opacities.

There are several basic types of cataracts including congenital cataracts; traumatic cataracts caused by accidental injury; and most common of all, senile cataracts, most prevalent in the elderly. It is not known why senile cataracts develop and the process may proceed over a period of months or even years before treatment is required. At present, the only successful treatment is surgical excision and replacement of the cataractous lens.

The lens of the human eye contains a hard central nucleus within a cortex. Disruption of the perfectly aligned fibers of the cortex and nucleous causes opacities. Large areas of the cortex and nucleus thus gradually become opaque until the image on the retina is blurred. At this point, the cataract has progressed to a stage where some of the resolving power of the eye is lost due to the damage to the lens.

A cataract is treated by relatively simple surgery under local anesthesia in which the lens material affecting vision is removed. Approximately one half million Americans undergo such surgery every year; this being the most common operative procedure performed by ophthalmic surgeons in the United States.

During the operation, the surgeon views the operation site through a high powered microscope which greatly magnifies the lens of the eye to facilitate the procedure. The eye is kept moist with physiological saline throughout the procedure.

In the past, standard procedure for removing the damaged lens involved first dilating the pupil and then making a half circle incision at the junction of the sclera and the clear cornea. The upper half of the cornea is reflected and the iris is retracted to provide access to the entire lens. The lens was then removed by one of several techniques. For example, the lens may be drawn or eased out through the incision by means of a cup-shaped instrument called an erysiphake. The lens may also be removed by a cryoadhesion (freezing) technique known in the art. Such procedures are known as intracapsular techniques, since the lens capsule remains intact.

Another method is to excise the anterior capsule, shell out the nucleus, and vacuum out the cortex. This is an extracapsular technique.

Regardless of the technique of removing the lens, the incision must be large enough for this purpose and must be sutured to complete the operation. The patient requires from about 48 hours to one week to convalesce from such operations due to the discomfort and irritation caused by the large incision.

In recent years intraocular lenses have been developed for implantation in the eye after the cataractous or otherwise damaged lens has been removed, thereby eliminating the need for contact lenses or eyeglasses after surgery.

The first intraocular lens was implanted in a human eye in 1949. From its inception, the intraocular lens has had a tumultuous history. The controversy has centered around the placement, location, design and surface quality of the artificial lenses.

THE PRIOR ART

Existing intraocular lenses are made of a clear, hard plastic material or glass, usually plano-convex. Such lenses are ground and polished to predetermined specifications determined for each individual prior to implantation. Over the years such lenses have had a broad range of forms and sizes. Basically, such lenses are a disc with or without supsensory projections about its periphery. The projections, in whatever form, suspend the lens within the anterior or posterior chamber. Such projections are commonly called haptic loops. These loops emanate from the periphery of the optic or clear portion of the lens. Such haptic loops may be curved, or be in the form of J's, or take almost any configuration, at each end of the lens. The thin loops can be made of prolene (polypropylene) and fit into holes in the disc or lens. The lens is then heat treated thereby expanding the loops to permanently attach them to the lens.

Whatever form the lens takes, it must be oriented along the visual axis within the eye. The visual axis is an imaginary line which passes axially through the center of the lens and extends through the pupil and cornea. The lens must be centrally oriented along this axis in the path of the light to the retina. The curved front and back surfaces of the lens or disc must be positioned on the same axis to provide an optically correct orientation. The purpose of the haptic loops is to anchor the lens in a central position along the visual axis. The curved portions of the loops contact the chamber walls and hold the lens in place. Lenses without supporting loops are designed to be held in place by their edges. However, this is less satisfactory, since position of the lens is not firmly anchored, and is subject to alteration.

The original intraocular lenses posed many problems associated with their use. Many such lenses, having loops of nylon or of plastic also showed marked biodegradation of the loops, after prolonged periods of use, where the chamber angle was contacted due to the chemical reaction between the loop material and adjoining structures. Many loops were digested completely leaving the lens free floating in the chamber and no longer aligned in the visual axis. Other problems occurred as the result of the surface finish on many of the early implants. Analysis showed sharp grooves in the surfaces formed from lathe polishing. Edge aberrations of the lenses also caused chronic irritation. It was also found that lenses of too large or too small a size caused corneal dystrophy. Examination of these early lens implants paved the way for the current knowledge of design requisites for intraocular lenses. Today, half the cataract operations performed in the United States involve implanting the newly perfected intraocular lenses.

Cataract surgery incorporating implantation of an intraocular lens is similar to the operation performed without implantation. However, there is no single method followed by all surgeons. Generally, a large incision, approximately 10 mm, is made in the conjunctiva and limbus where the cornea and the sclera meet. The cataractous lens nucleus is then shelled out. The remaining cortex is aspirated to leave a clear lens capsule. A relatively new process called phaco-emulsification allows this incision to be reduced to 3 mm. Phaco-emulsification, an extracapsular technique involves ultrasonic fragmentation of the lens into small particles. Once this has been accomplished, the particles are removed by suction leaving a clean capsule free from cataractous material, and only a small opening in the eye. However, the present relatively large-sized implants require enlarging the incision to at least 7 mm to accommodate the introduction of the intraocular lens. The lens is place and positioned in the posterior chamber to provide an optically correct visual axis. The loops rest and anchor the lens against the capsule walls. Positioning the lens is a delicate technique and surgeons use differing lenses and procedures.

While intraocular lenses are becoming popular in present day ophthamology, many designs are still experimental and it is not known how long the new lenses will last in the human eye. Ophthamologists usually suggest that older patients have the lens implant. Controversy still remains as to the design and placement of the lens. Aphakic patients must still go through this intricate operation to accurately position the lens and must still convalesce for many days until the incision heals.

Furthermore, by virtue of the hard plastic composition and large size of presently available intraocular lenses, they are difficult to grasp and maneuver into their proper position. The haptic loops emanating from the lenses are also awkward to manipulate and may cause trauma to the eye if not handled properly.

The initial incision in the cornea still tends to be large, sometimes more than 7 mm, to accommodate the lens and the protruding loops. The lens is slipped through the large incision, loop end first, and positioned in the posterior chamber. An incision of this size requires post operative care and causes irritation and consequent discomfort to the patient.

In view of the foregoing, it is apparent that the need for heavy glasses or contact lenses after cataract surgery has been eliminated. However, serious problems still exist with the lenses themselves and also with the operating procedures. A considerable body of patent art exists in this field of which the following is representative.

Thiele, U.S. Pat. No. 3,553,299 issued Jan. 5, 1971, describes a process for making replacement eye lenses by dissolving the lenses of the eyes of warm blooded animals and processing the resulting material to form a gel from which the replacement lens is formed.

Cordrey et al U.S. Pat. No. 3,943,045 issued Mar. 9, 1976, describes a process for making hydrophilic polymers suitable for use as contact lenses or surgical implants, among other things. Highgate, U.S. Pat. No. 3,961,379 issued June 8, 1976, also discloses hydrophilic polymers such as polymethyl methacrylate and hydroxyethyl methacrylate which are suitable for use in making contact and prosthetic lenses.

Flom, U.S. Pat. No. 3,991,426 issued Nov. 16, 1976 describes artificial intraocular lenses for implantation in the posterior chamber of the eye. This reference also summarizes in considerable detail the history and development of artificial intraocular lenses and the need for them.

Banko, U.S. Pat. No. 4,253,199 issued Mar. 3, 1981 discloses deformable lenses for surgical implantation which are composed of a hydrophilic acrylic polymer, such as "Hydron", which is used for soft contact lenses. The lenses are filled with a suitable liquid or semi-viscous material such as a sterile solution or gelatin, or Ringer's solution, and sealed prior to implantation.

Tennant U.S. Pat. Nos. 4,254,509 and 4,254,510, each issued Mar. 10, 1981, disclose artificial intraocular lenses composed of rigid materials such as polymethyl methacrylate or soft materials such as hydroxyethyl-methacrylate; the rigid material being used for the lens only or for the entire implant and the soft material being used only for the supporting members in other embodiments.

The entire disclosures of U.S. Pat. Nos. 3,943,045; 3,961,379; 3,991,426; 4,253,199; and 4,254,509 are hereby incorporated herein by reference.

It is apparent from the foregoing, that while much work has been done in this art, there still remains a need for an improved intraocular lens and an improved, less traumatic procedure for the implantation of such lenses.

It is a primary object of the present invention, therefore, to provide an improved intraocular lens which overcomes the aforementioned problems of the prior art.

More specifically, it is an object of the invention to provide an intraocular lens which does not require permanent or long lasting positioning means but which is self-positioning in the optic axis within a relatively short period.

It is another object of the invention to provide an improved intraocular lens which employs only very temporary positioning means until such time as it is self-positioning.

It is still another object of the invention to provide an improved intraocular lens and method for its implantation which reduces the size of the incision required and thus trauma to the eye and consequently reduces convalescent time and discomfort to the patient.

It is a further object of the present invention to provide an intraocular lens which expands after implantation to form a soft lens with soft haptic loops incapable of damaging the capsule interior and which is thus suspended centrally along the visual axis of the eye.

SUMMARY OF THE INVENTION

The foregoing and other objects of the invention, which will become apparent below, are achieved by providing an improved artificial intraocular lens which is capable of implantation through a much smaller incision than was previously required and which requires either none or only very temporary, non-traumatic support or positioning means, since the lens is self-supporting and self-aligning on the optical axis after a very short time.

The new artificial intraocular lenses, while composed of materials previously available and used in this art, are designed to make use of a property of these materials in a novel way which was not previously recognized in the art. More specifically, the new lenses are designed and formed to take advantage of the hydration of hydrophilic materials so that they swell and expand in size. This permits the new lenses, prior to implantation, to be much smaller than the natural lens or any previous artificial lens, since they are hydrated by the fluid present in the normal eye so that they expand to the predetermined desired optically correct size. The new lenses are composed of a dry, solid hydrophilic material capable of hydration and have a minimum diameter of about 2 mm and a maximum diameter of only about 5 mm in the dry state, which is less than the diameter of the natural lens. This permits the implantation of the new lenses through an incision corresponding to the 5 mm maximum diameter, at most, and in some cases through an incision of only about 2 mm. This compares to the lenses of the prior art which required an incision of at least 7 mm and up to 12 mm or more. It is clear, therefore, that the surgical trauma is greatly reduced, correspondingly reducing discomfort and convalescent time.

The new lenses are formed of hydrophilic materials capable of hydration by the fluid present in the eye to a final diameter of from about 6 mm to about 14 mm to provide the predetermined, optically correct lens for the particular patient. Depending upon the particular hydrophilic material employed, the expansion on hydration varies from about 1.5 to about 3, or even up to about 20 diameters. Also depending on the particular hydrophilic material employed, the time required for full hydration and expansion varies from about 1 hour up to about 24 hours or somewhat longer.

Inasmuch as the dry lens prior to implantation is smaller than the posterior cavity vacated by the damaged lens, it is preferred, but not essential, to provide temporary support or positioning means to align the lens on the optic axis until it hydrates and expands to fill the posterior cavity, thus becoming self supporting and self aligning. In one embodiment, the intraocular lens in its pre-implantation, dry form is a disc having two or more suspensory haptic loops formed integrally with and projecting from the periphery of the disc, with the ends of the loops curved towards the disc proper. These curved portions of the haptic loops, rest against the chamber walls of the capsule after implantation to anchor the lens in position on the optic axis. As the lens is hydrated by the natural fluid in the eye, it expands and the haptic loops collapse inwardly and nest against the lens.

In other embodiments of the invention, the haptic loops or other support are temporary being composed of biodegradable materials which are absorbed and disappear shortly after the lens has fully expanded and become self-supporting and self-aligning. Of course, longer lasting or even permanent haptic loops or other support means made, for example, of polypropylene may be employed, but this is, of course, not preferred, since the disadvantages of such prior art support means would not be eliminated.

The recently developed techniques for removing the damaged natural lens by phaco-emulsification or ultrasonic fragmentation are, or course, necessarily used to gain the advantages of the new minimal diameter lenses and incisions.

The procedure for implantation of the new lenses in their hardened dry state is similar to those previously discussed but includes various improvements. The intitial incision made in the cornea of about 2-3 mm is considerably smaller than is possible with prior techniques. A small phaco-needle is inserted through the incision to phaco-emulsify the cataractous lens and remove it by suction, leaving the lens capsule intact. The hard, dehydrated intraoculare lens is then inserted through the small incision and implanted in the posterior chamber. The haptic loops if any, fit in the lens capsule and hold the intraocular lens in a central position to provide an optically correct visual axis.

At this point, the intraocular lens is bathed by the aqueous humor which fills the anterior chamber of the eyeball. One particular hydrophilic material expands to approximately 179% its original diameter for example. Therefore, if the lens in its dry state is 4 mm, it will swell or expand to 7 mm. The lens will swell to its soft hydrated form in approximately 24 hours when made of this material. The lens expands to a size larger than the incision site to provide an optically correct visual axis with sufficient size to avoid spherical and edge aberrations. The small incision is then sutured.

A hydrophilic intraocular lens offers many advantages compared to present day lenses. The small size of the dry lens before and during surgery permits easy maneuverability and handling. The small incision causes lens irritation and quicker healing. Usually patients are discharged on the same day as the operation. Furthermore, the haptic loops carved from the lens periphery, also being hydrophilic, expand after insertion. Thus, the loops initially support the lens in its hardened state within the capsule; however, as the lens and loops begin to expand, the loops contract circumferentially toward the disc periphery. In other words, the lens expands to fill the chamber while being maintained along the visual axis by the haptic loops.

The loops, being of the soft plastic material conform to the capsule wall. The integral loops will not disengage from the lens body leaving a free floating disc in the chamber as with some previous lenses.

The soft hydrated lens also has smooth soft edges less likely to cause discomfort and infection than hard lenses.

In the manufacture of the new lenses, the hydrophilic material in its dry hardened state is formed into rods which are cut into pellets. The pellets are then lathe cut into fine discs, leaving enough material to form or carve the loops from the disc periphery. The discs are then tumble polished to provide a smooth surface finish. The optic power is ground into the lens depending on the size or depth of the eye and the curve of the front of the eye. These specifications are determined for each individual patient by the physician by standard examination and calculation. They can be injection molded or spin cast.

The lenses may also be made by injection molding, spin casting, or any other suitable method.

Virtually, any of the many hydrophilic materials known to the art for use in soft contact lenses, intraocular lenses or other surgical implants may be used if they have suitable optical properties, are capable of being formed into the new lenses, and are capable of hydration in the eye to expand as necessary in the present invention. In addition to the polymethyl methacrylate and hydroxyethyl methacrylate, a hydrophilic acrylic polymer available commericially under the trademark "Hydron" is especially preferred.

BRIEF DESCRIPTION OF THE DRAWINGS

These and other objects of the present invention are hereinafter more fully set forth with reference to the accompanying drawings wherein.

DETAILED DESCRIPTION OF THE PREFERRED EMBODIMENT AND METHOD

Figure 1:
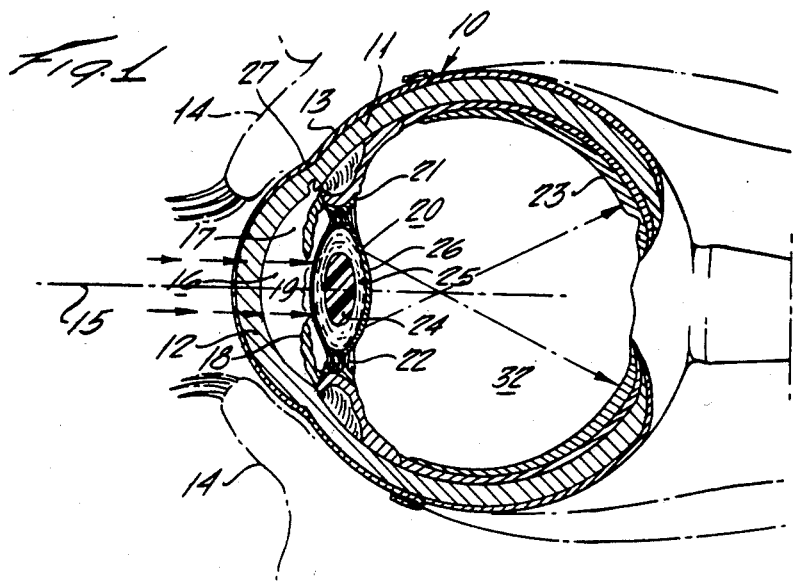
FIG. 1 is a side elevational view, in half section, of a human eye with a normal lens focusing light rays on the retina.

Referring now to the drawings, and particularly to FIG. 1 thereof, the basic parts of the normal human eyeball are illustrated. The eyeball 10 contains a lens 20. The outer coating or white of the eye is called the sclera 11. The central portion of the sclera has a clear outer coat called the cornea 12, which is the most sensitive part of the eye.

Starting at the edge of the cornea 12 and covering the sclera 11 is a thin, transparent membraneous layer called the conjunctiva 13. The conjunctiva also folds backward to line the eyelids 14 so that the two surfaces glide over one another when the lids blink or the eye moves.

The anterior chamber 16 directly behind the cornea and the front portion of the eyeball, contains an aqueous fluid called the aqueous humor 17 which circulates nourishment and maintains the correct pressure in the eye.

The iris 18, the colored portion of the eye, is located at the back of the anterior chamber 16. The iris 18 surrounds a central opening called the pupil 19. The muscles of the iris 18 dilate and contract the pupil 19 thereby regulating the amount of light entering the eye.

Behind the iris 18 is the crystalline lens 20 of the eye which in a normal eye is clear, but cloudy if cataractous. A ring-like structure behind the outer edge of the iris 18, called the cilliary body 21, focuses the lens and manufactures the aqueous humor. Zonules 22 stretch from the ciliary body 21 to the lens 20 and hold it in place.

The back portion of the eye contains a large space between the lens 20 and the retina 23. This space contains a jelly-like fluid called the vitreous humor 32 which also maintains the correct pressure within the eye.

As seen in FIG. 1, the lens 20 consists of a hard inner nucleus 24 surrounded by jelly-like fibers called the cortex 25. The lens 20 and cortex 25 are encased in a thin elastic elliptically-shaped membrane called the lens capsule 26. The cortex 25 is generally the portion of the lens which becomes cloudy with the onset of cataracts.

Initially, opacity appears in a spoke-shaped pattern developing at the front and back of the lens capsule 26. The opacity gradually spreads towards the center of the lens 20 during a period of many years. Eventually larger and larger areas of the cortex 25 become opaque until the iris casts no shadow. At this stage vision is completely lost and the cataract is said to be mature. A mature cataract is more easily separated from the lens capsule 26 than in its early development.

Figure 2:
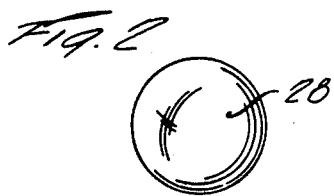
FIG. 2 is a top plan view of a lens of the invention without haptic loops prior to implantation.

FIG. 2 illustrates the intraocular lens of the present invention in its dehydrated form 28. The lens is implanted through a small incision in the limbus 27 and positioned within the open side of the lens capsule 26.

Figure 2A:
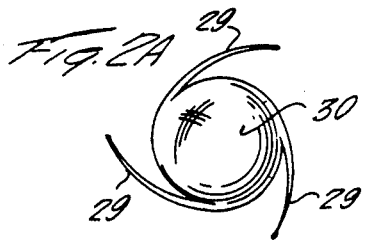
FIG. 2A is a top plan view of a lens of the invention, with haptic loops carved from the lens disc, also prior to implantation.

The dry hardened plastic disc 28 is composed of a suitable hydrophilic material, which is ground to the predetermined optical power required by the cataract patient. The disc or lens 28 is tumble polished to ensure a smooth surface finish. Enough material may be left on the disc periphery to form tangential haptic loops 29 of the same hydrophilic material, as shown in FIG. 2A. As noted above, it is preferred to omit haptic loops altogether and rely on the expansion of the hydrophilic lens to align the lens on the optical axis and become self-supporting in the posterior chamber. It is, however, entirely acceptable to use hydrophilic haptic loops 29 or even temporary biodegradable haptic loops. While less desirable, permanent polypropylene haptic loops may also be employed.

Consider now the surgical procedure involved in implantation of the intraocular lens of the present invention. The surgeon is aided by a high powered microscope, and views the implantation site through magnified eyes. A 3 mm incision, for example, is made in the limbus 27. The phaco-emulsification probe or needle is inserted through the incision and contacts the lens 20 through the pupil 19 which has been dilated. The probe shatters the lens 20 and removes the nucleus 24 and the cortex 25 leaving the capsule 26 intact.

The surgeon guides the small hardened intraocular lens 28 through the incision in the limbus. The intraocular lens 28 travels into the posterior chamber 16 through the dilated pupil 19. Once through the pupil 19, one of the haptic loops 29, if present, is fitted against the wall of the lens capsule 26. The surgeon delicately maneuvers the opposing loop or loops 29 against the opposite wall of the lens capsule 26. The intraocular lens 28 is now suspended within the capsule 26 by the haptic loops 29 which position it on the optical axis 15. The incision is the sutured.

Figure 3:
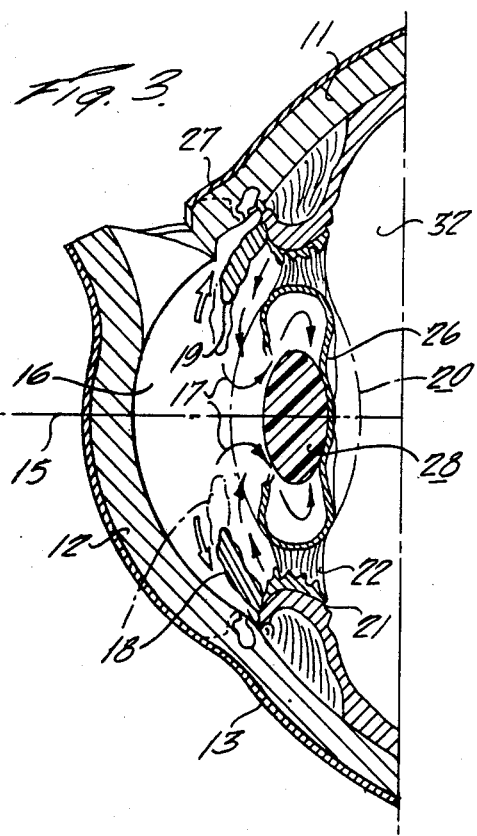
FIG. 3, is a side elevational view, in half section, of a human eye from which the natural lens has been removed showing a lens of the invention in its dry state immediately after implantation in the posterior cavity.
Figure 4:
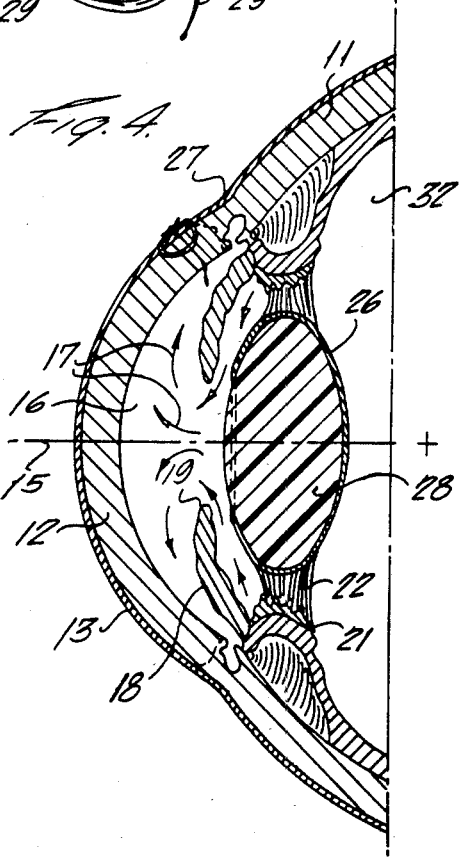
FIG. 4, is a side elevational view of the eye of FIG. 3 after the implanted lens of the invention has hydrated and expanded to fill the posterior cavity and align itself on the optic axis.

The dry intraocular lens 28 is now immersed in the aqueous humor solution 17 of the eye. The hydrophilic lens begins to expand or swell until it reaches its maximum size shown in FIG. 3 within about 2 to about 24 hours after being implanted so that it completely fills the capsule 26. The haptic loops 29 as they expand circumferentially contract towards the periphery of lens 30 and are thus pushed toward the capsule wall.

The intraocular lens 30 is now a soft expanded disc of sufficient size to avoid spherical and edge aberrations and is positioned on the optical axis 15.

In the preferred embodiment of the present invention, the lens 28 without haptic loops expand after implantation to substantially fill the capsule and is self-centering on the optic axis 15. However, haptic loops 29 of the same hydrophilic material as the lens or a biodegradeable material may be employed which function during initial implantation and the expansion or swelling of the lens in the capsule to center and insure retention of the lens in the capsule. The loops also soften or degrade and nest on the periphery of the lens as the lens expands to fill the capsule 26 without causing trauma or irritation to the capsule tissue.

EXAMPLE I

Dry, solid hydrophilic rods of "Hydron" acrylic polymer, for example, are cut into pellets which are then lathe cut into discs. The patient's corneal curve may, for example, measure 4150 diopters with an axial length of 24 mm. In this case, by calculation using known fomulas, the disc would suitably be ground to an optical power of 19.4 diopters. Two or more haptic loops may be carved from the disc periphery emanating from opposite positions. The disc or lens is then tumble polished to provide a smooth surface finish absent any spherical or edge aberrations.

The patient's eyelids are spread open using an eyelid speculum. The area around the eye is injected with xylocaine to immobilize the muscles. Lidocaine is administered in drops to numb the eyeball. The patient's eye is placed directly below a high powered microscope so that the operation site is magnified.

An incision approximately 3 mm wide is made in the conjunctiva and limbus (where the cornea and sclera meet) exposing passage to the crystalline lens of the eye through the pupil region. The incision and eye are kept moist with a saline solution throughout the operation.

The vibrating needle cuts the lens material into small particles that are aspirated through the needle. The remaining lens cortex material is then aspirated leaving the lens capsule intact.

The surgeon manipulates the lens through the incision into the pupilary area. The lens is then positioned in the center of the capsule with a loop supporting the lens on opposite sides of the capsule wall. The limbal incision is then sutured.

Within 24 hours the 4 mm lens will expand to over 7 mm to provide an optically correct visual axis with sufficient size to avoid spherical and edge aberrations. The expanded soft lens will fill the capsule bag and be centered by the haptic loops in the visual axis.

The expanded intraocular lens has a soft surfce finish of the required optical power needed for the patient to regain perfect vision. Thus, the patient will be able to see and leave the hosptial soon after the operation.

As noted above, while "Hydron" hydrophilic acrylic polymer is preferred as the lens material, a wide variety of other commericially available hydratable polymers may be used, including those now used in soft contact lenses. Commercially available materials previously approved for use in soft contact lenses, and which are also suitable for use in the lenses of this invention, include the following:

| Materials Approved For Use As Soft Contact Lenses | | | |
|---|---|---|---|
| Name | Type | Manufacturer | Trade Name |
| Bufilcon A | hema | Burton Parsons | |
| Cabufocon A | CAB | Danker-Wohlk | Meso-lens |
| Crofilcon A | hema | Corneal Sciences | |
| Dimefilcon A | hema | Calcon Labs | Gelflex |
| Droxafilcon A | hema | Opthalmos | Hydralens |
| Etafilcon A | hema | Frontier c/l | Hydro-marc |
| Hefilcon A | hema | Automated Optics | PHP |
| Lidofilcon A | vinyl | CLM | Sauflon 70 |
| Lidofilcon B | vinyl | CLM | Sauflon 85 |
| Mafilcon A | hema | N & N/Menicon | |
| Ocufilcon A | hema | Urocon Int | Tresoft/Urosoft |
| Phemfilcon A | hema | Wesley-Jessen | Durasoft/Phemecol |
| Polymacon | hema | Bausch & Lomb | Soflens |
| Porofocon A | CAB | Rynco Scientific | Rx-56 |
| Porofocon B | CAB | Soft Lenses, Inc. | CAB-Curve |
| Tetrafilcon A | hema | UCO Optics | Aquaflex/Aosoft |
| Vifilcon A | hema | Warner Lambert | Softcon |

More specifically, recently developed materials which are hydratable and otherwise suitable for use in the new lenses include, for example, a copolymer of glyceryl methacrylate and methyl methacrylate (MMA) available from Corneal Sciences, Inc. of Boston, Mass. Soft contact lenses made with this material leave a water content of 41–42% and may be worn continuously.

A series of suitable hydrogels produced by Union Optics Corporation are derived from a hydrophobic monomer, glycidyl methacrylate, which is copolymerized with methyl methacrylate and other monomers to provide a hydratable polymer.

Other suitable hydrogel copolymers include a terpolymer of acrylic acid, N-(1,1-dimethyl-3-oxobutyl) acrylamide, and methyl methacrylate. A hydrogel copolymer of an acrylomide derivative, N,N-dimethylacrylamide, and methylmethacrylate, or similar alkyl derivatives, is also useful.

Copolymers of hydroxyethyl methacrylate (HEMA) and vinyl acetate, and terpolymers of these materials with acrylamide derivatives are also useful.

Copolymerization of MMA (80–90%) with acrylic acid (10–20%), and diverse cross-linking agents, followed by neutralization of the polymerized acrylic acid with a basic substance, such as ammonium hydroxide and ethylenimide yield hydrogels useful for contact lenses. The depth of penetration of the neutralizing agent into the polymer determines the hydration of the lens.

Finally, a hydrogel contact lens which is not made from the familiar acrylic monomers, and does not contain VP either, is Optamol which is advertised as an allyloxy polymer derivative and appears to be a copolymer of ally 2-hydroxyethyl ether suitable for use in this invention.

In a preferred embodiment of the invention, commercially available hydrated polymers of the type described above are further purified to remove chemical impurities by soaking them in a saline bath for a suitable period of time and then dehydrating them by freeze drying according to procedures known per se to produce dry, but hydrated polymers from which the new lense may be fashioned. This operation may be performed either before or after shaping of the lens.

Even though particular embodiments of the invention have been illustrated and described herein, it is not intended to limit the invention and changes and modifications may be made therein within the scope of the claims presented. Thus, the lens of the present invention may be of shapes and configurations other than those illustrated; for example, it may be oval or elliptically shaped having a minor axis of small dimension to fit through a small incision and major axis of greater dimension of a size generally equal to the lens capsule so that the lens is self-supporting upon initial positioning in the lens capsule thereby obviating the need for haptic loops or the like.

What is claimed is*

1. In an artificial intraocular lens for surgical implantation to replace a damaged natural lens in an otherwise functional eye of a patient, the improvement which comprises:

said artificial lens having a cross sectional dimension substantially less than that of the natural lens, and being composed of a dry, solid hydrophilic material capable of hydration by the natural fluid present in the eye to expand after implantation to provide an optically correct lens;

to thus improve the vision of the patient.

2. An artificial intraocular lens of claim 1 having a minimum diameter of about 2mm and a maximum diameter of about 5 mm prior to implantation.

3. An artificial intraocular lens of claim 1 wherein the diameter of the lens after implantation, hydration and expansion is about 1.5 to about 20 times the diameter of the lens prior to implantation.

4. An artificial intraocular lens of claims 1, 2, 2 or 3, having means for supporting said lens in the posterior chamber of the eye.

5. An artificial lens of claim 4 wherein the support means are temporary.

6. An artificial lens of claim 5 wherein the support means are bio-degradable.

7. An artificial lens of claim 4 wherein the hydrophilic material is selected from the group consisting of hydroxyethyl methacrylate, and "Hydron" hydrophilic acrylic polymer.

8. An artificial lens of claim 1 wherein the hydrophilic material is hydroxyethyl methacrylate.

9. An artificial lens of claim 1 wherein the hydrophilic material is Hydron hydrophilic acrylic polymer.

10. An artificial lens of claim 1 wherein the hydrophilic polymer hydrates after implantation to increase the diameter of the lens from about 1.5 to 20 times its diameter prior to implantation.

11. In a method for the surgical implantation of an artificial intraocular lens to replace a damaged natural lens in an otherwise functional eye of a patient, the improvement which comprises:

implanting an artificial lens having a minimum diameter substantially less than that of the natural lens and being composed of a dry, solid hydrophilic material capable of hydration by the natural fluid present in the eye to expand after implantation to provide an optically correct lens;

said implantation of the dry lens being made through an incision of minimal width corresponding substantially to the diameter of said dry lens.

12. The method of claim 11 wherein the minimum diameter of the lens and incision is about 2mm and the maximum diameter of the lens and incision is about 5 mm.

13. The method of claim 12 wherein the lens after implantation expands to a diameter of from about 6 mm to about 14 mm.

14. An artificial intraocular lens of claim 1, 8, or 9, wherein the hydrophilic material has been subjected to a saline bath and freeze dried to remove chemical impurities.

* * * * *

UNITED STATES PATENT AND TRADEMARK OFFICE
CERTIFICATE OF CORRECTION

PATENT NO. : 4,556,998

DATED : December 10, 1985

INVENTOR(S) : Steven B. Siepser

It is certified that error appears in the above-identified patent and that said Letters Patent is hereby corrected as shown below:

Col. 2, line 43; "supsensory" should be --suspensory--
Col. 6, line 10; "or course" should be --of course--
Col. 6, line 21; "intraoculare" should be --intraocular--
Col. 6, line 42; "lens" should be --less--
Col 11, line 31; "1, 2, 2 or 3" should be 1, 2 or 3
Col 12, line 33; "1, 8 or 9" should be -- 1, 8 or 9.

Signed and Sealed this

Fifteenth Day of July 1986

[SEAL]

Attest:

DONALD J. QUIGG

Attesting Officer

Commissioner of Patents and Trademarks

Notice of Adverse Decision in Interference

In Interference No. 101,837, involving Patent No. 4,556,998, S. B. Siepser, ARTIFICIAL INTRAOCULAR LENSES AND METHOD FOR THEIR SURGICAL IMPLANTATION, final judgment adverse to the patentee was rendered Jan. 22, 1990, as to claims 1-14.
( *Official Gazette May 8, 1990* )